US00PP12982P2

(12) United States Plant Patent
Billingsley et al.

(10) Patent No.: US PP12,982 P2
(45) Date of Patent: Sep. 17, 2002

(54) HYDRANGEA PLANT NAMED 'VAUGHN'S LILLIE'

(75) Inventors: William Vaughn Billingsley; Lillie Billingsley, both of Rabun Gap, GA (US)

(73) Assignee: Billingsley Wholesale Nursery, Inc., Rabun Gap, GA (US)

( * ) Notice: Subject to any disclaimer, the term of this patent is extended or adjusted under 35 U.S.C. 154(b) by 39 days.

(21) Appl. No.: 09/840,809

(22) Filed: Apr. 25, 2001

(51) Int. Cl.[7] ..... A01H 5/00
(52) U.S. Cl. ..... Plt./250
(58) Field of Search ..... Plt./250

*Primary Examiner*—Bruce R. Campell
*Assistant Examiner*—Annette H. Para
(74) *Attorney, Agent, or Firm*—C. A. Whealy

(57) ABSTRACT

A distinct cultivar of Hydrangea plant named 'Vaughn's Lillie', characterized by its growth habit; short internodes; large conical to rounded inflorescences; showy white-colored sepals; and long flowering period.

1 Drawing Sheet

BACKGROUND OF THE INVENTION

The present Invention relates to a new and distinct cultivar of oakleaf Hydrangea plant, botanically known as *Hydrangea quercifolia*, and hereinafter referred to by the name 'Vaughn's Lillie'.

The new Hydrangea originated from a cross by the Inventors of two unnamed selections of *Hydrangea quercifolia*, not patented. The cultivar Vaughn's Lillie was discovered and selected by the Inventors in 1994 as a single plant within the progeny of the stated cross in a controlled environment in Rabun Gap, Ga. The new Hydrangea was selected on the basis of its compact plant habit, large showy sterile inflorescences, and long flowering season.

Asexual reproduction of the new cultivar by cuttings taken at Rabun Gap, Ga., since 1994, has shown that the unique features of this new Hydrangea are stable and reproduced true to type in successive generations.

SUMMARY OF THE INVENTION

Plants of the cultivar Vaughn's Lillie have not been observed under all possible environmental conditions. The phenotype may vary somewhat with variations in environment such as temperature, light intensity, daylength, irrigation amount and frequency, and fertilizer type and rate without, however, any variance in genotype.

The following traits have been repeatedly observed and are determined to be the unique characteristics of 'Vaughn's Lillie'. These characteristics in combination distinguish 'Vaughn's Lillie' as a new and distinct cultivar:

1. Compact growth habit.
2. Short internodes.
3. Large conical to rounded inflorescences.
4. Showy white-colored sepals.
5. Long flowering period.

Compared to plants of the parent selections, plants of the new Hydrangea are more compact and have much shorter internodes.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new Hydrangea. The photograph comprises a side perspective view of a typical three-year old plant of 'Vaughn's Lillie'.

DETAILED BOTANICAL DESCRIPTION

In the following description, color references are made to The Royal Horticultural Society Colour Chart except where general terms of ordinary dictionary significance are used. Plants were grown in Rabun Gap, Ga. under outdoor conditions which closely approximate commercial production conditions. Plants used for the description were grown in the ground and were about three years old.

Botanical classification: *Hydrangea quercifolia* cultivar Vaughn's Lillie.

Parentage:

*Male, or pollen, parent*.—Unnamed *Hydrangea quercifolia* selection, not patented.

*Female, or seed, parent*.—Unnamed *Hydrangea quercifolia* selection, not patented.

Propagation:

*Type cutting*.—By cuttings.

*Time to rooting*.—About 4 to 6 weeks.

*Roots description*.—Freely branching, fibrous.

Plant description:

*Form*.—Upright and broadly rounded plant habit; compact and uniform; short internodes, dense and bushy perennial shrub.

*Plant height*.—About 68.6 cm.

*Plant diameter or area of spread*.—About 81.3 cm.

*Branching habit*.—Freely branching with about 15 to 20 lateral branches per plant.

*Lateral branches*.—Length: About 15 to 60 cm. Diameter, below first set of opposite leaves: About 3.2 to 9.5 mm. Internode length: About 1.9 to 3.8 cm. Texture: First year stems: Dense matted pubescent.

Older stems: Glabrous; bark exfoliates into papery sheets. Color: First year stems: Pubesence covers stem, 165B. Older stems: 174D to 166B.

*Buds*.—Length: About 6.3 mm. Diameter: About 3 to 4 mm. Shape: Ovoid, flattened. Texture: Covered with matted pubescence. Color: 174D.

*Foliage description*.—Leaves simple, opposite, generally symmetrical and long persisting. Quantity per lateral branch: About 20 to 30. Length: About 8.9 to 17.8 cm. Width: About 8.25 to 15.2 cm. Angle: About 60 to 90° from vertical. Shape: Roughly ovate, five-lobed. Apices, terminal and lobe: Abruptly acuminate. Base: Truncate to semi-cordate. Margin: Sharply serrate; lobes entire. Sinuses: Divergent, C-shaped. Texture: Young leaves: Upper surface, pubescent; lower surface, tormentose-pubescent. Fully expanded leaves: Upper surface, minutely pubescent; lower surface, heavily pubescent. Color: Young foliage, upper surface: 191C; veins covered with pubescence, 165B. Young foliage, lower surface: 192C; veins covered with pubescence, 165B. Mature foliage, upper surface: 137A; in Rabun County, Ga., in the autumn, leaves turn dark purple, 187A, fall color persists for about 3 to 4 weeks. Mature foliage, lower surface: 191C. Petiole: Length: About 3.8 to 7.6 cm. Diameter: About 2 to 3 mm. Color: Covered with brown, 165B, wooly pubescence.

Flower description:

*Flower type and habit*.—Single flowers densely arranged on dense compact panicles with large showy sepals. Calyces persistent. Not fragrant.

*Natural flowering season and flower longevity*.—Long flowering season, in Rabun County, Ga., flowers open in June and are colorful into July. Flowers continuous during the summer and fall, occasionally until October.

*Flower longevity*.—Individual flowers last about 2 months on the plant.

*Quantity of flowers*.—Freely flowering; up to eight inflorescences per lateral branch with about 75 to 125 flowers per panicle.

*Inflorescence length*.—About 10.2 to 12.7 cm.

*Inflorescence diameter*.—About 10.2 to 12.7 cm.

*Flower diameter*.—About 2 cm.

*Flower buds*.—Length: About 6 to 8 mm. Diameter: About 3 to 4 mm. Shape: Ovoid. Texture: Covered with matted pubescence. Color: 174D.

*Petals*.—Not observed.

*Sepals*.—Arrangement: About 4 in a single whorl. Length: About 6.4 to 9.5 mm. Width: About 1.3 to 1.6 cm. Apex: Obtuse. Base: Rounded. Margin: Entire. Color: When opening, upper and lower surfaces: Glistening cream-white, 155A; aging to brown, 165B. Fully opened, upper and lower surfaces: Glistening cream-white, 155A; aging to brown, 165B.

*Pedicels*.—Angle: About 30 to 60° from vertical. Strength: Moderate. Length: About 3.8 to 5.1 cm. Diameter: About 0.5 to 1 mm. Color: 155A.

*Peduncles*.—Angle: About 45 to 90° from vertical. Strength: Strong. Length: About 3 to 6 cm. Diameter: About 1 to 2 mm. Color: 155A.

*Reproductive organs*.—Not observed.

*Seed/fruit*.—Not observed.

Disease/pest resistance: Under commercial production conditions, plants of the new Hydrangea have not been observed to be resistant to pathogens or pests common to Hydrangea.

Hardiness: Plants of the new Hydrangea have been shown to be hardy to USDA Hardiness Zone 6 to 9.

It is claimed:

1. A new and distinct cultivar of Hydrangea plant named 'Vaughn's Lillie', as illustrated and described.

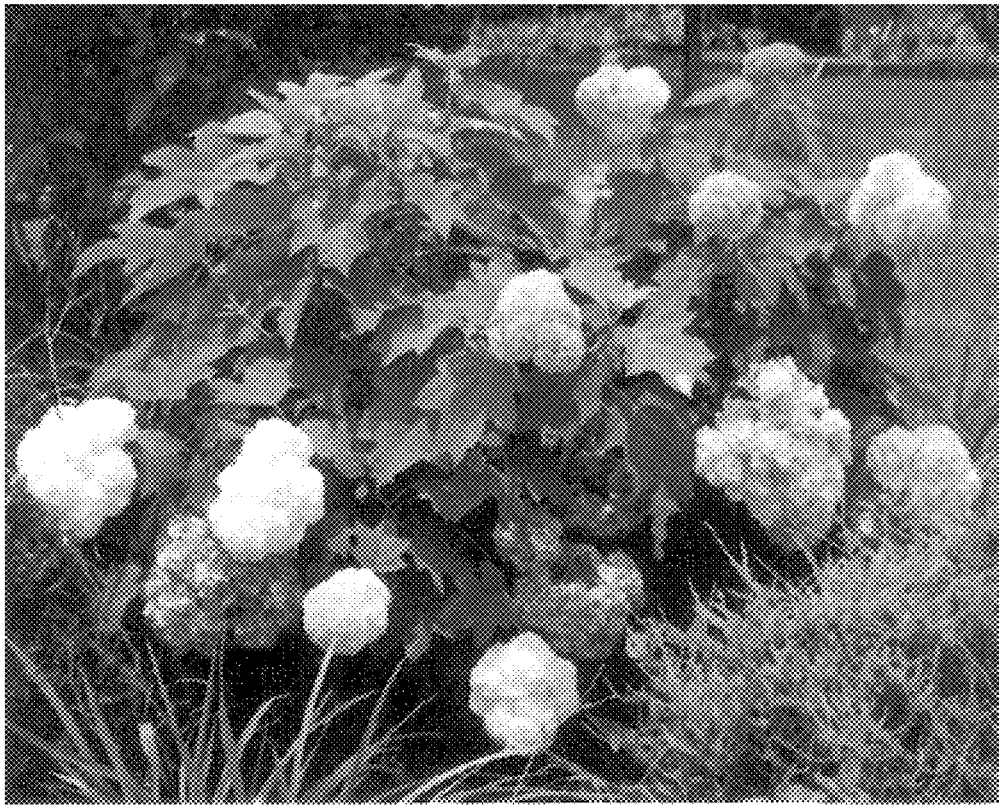

* * * * *